United States Patent [19]
Lotze et al.

[11] Patent Number: 5,635,044
[45] Date of Patent: Jun. 3, 1997

[54] ELECTRODE FOR ZIRCONIA OXYGEN SENSORS

[76] Inventors: Thomas H. Lotze, 11 Wildwood Dr., Fairfield, Ohio 45014; William Thompson, 3382 Sherbrooke Dr., Cincinnati, Ohio 45241; Theodore P. Berry, 8830 Weller Station Dr., Cincinnati, Ohio 45249

[21] Appl. No.: 514,024

[22] Filed: Aug. 11, 1995

[51] Int. Cl.⁶ ................................................ G01N 27/409
[52] U.S. Cl. .......................... 204/428; 204/424; 204/427; 205/784
[58] Field of Search ........................ 204/421–429

[56] References Cited

U.S. PATENT DOCUMENTS

| | | | |
|---|---|---|---|
| 3,645,875 | 2/1972 | Record et al. | 204/429 |
| 4,046,661 | 9/1977 | Stringer et al. | 204/422 |
| 4,101,404 | 7/1978 | Blumenthal et al. | 204/427 |
| 4,186,072 | 1/1980 | Blumenthal et al. | 204/427 |
| 4,193,857 | 3/1980 | Bannister et al. | 204/426 |
| 4,485,002 | 11/1984 | Wunning | 204/424 |
| 4,588,493 | 5/1986 | Blumenthal et al. | 204/428 |
| 4,592,825 | 6/1986 | Crevoiserat | 204/427 |
| 4,808,294 | 2/1989 | Beuret et al. | 204/427 |
| 4,814,061 | 3/1989 | Blumenthal et al. | 204/428 |
| 5,352,344 | 10/1994 | Gohring et al. | 204/427 |

*Primary Examiner*—T. Tung
*Attorney, Agent, or Firm*—Steven J. Rosen

[57] ABSTRACT

An oxygen sensor is provided with a virtual point contact electrode to improve performance, extend operational life and to minimize thermal shock breakage; it is also provided with reduced annular space between the protective sheath and zirconia electrolyte, and minimized communicating openings to the furnace atmosphere, in order to reduce burnoff air flow during probe conditioning.

8 Claims, 1 Drawing Sheet

ELECTRODE FOR ZIRCONIA OXYGEN SENSORS

BACKGROUND OF THE INVENTION

References Cited
U.S. PATENT DOCUMENTS

| | | | |
|---|---|---|---|
| 3,645,875 | 2/1972 | Record et al | 204/195 |
| 4,046,661 | 9/1977 | Stringer et al | 204/195 S |
| 4,101,404 | 7/1978 | Blumenthal et al | 204/195 S |
| 4,186,072 | 1/1980 | Blumenthal et al | 204/195 S |
| 4,193,857 | 3/1980 | Bannister et al | 204/195 S |
| 4,588,493 | 5/1986 | Blumenthal et al | 204/410 |
| 4,814,061 | 3/1989 | Blumenthal et al | 204/410 |

1. Field of the Invention

The invention is specifically designed to address problems related to measurement and control of carbon potential in furnaces, where special carbonaceous atmospheres are maintained in contact with (usually) ferrous materials at elevated temperatures. Diffusion of carbon into the work pieces is controlled to provide hardening and abrasion resistance in the surface of the part, in a process well known to those versed in the science. The patent describes design factors for improved reliability and maintenance of the zirconia oxygen sensor in this and related fields.

2. Description of Related Art

Since about 1970, rapid commercial development of electrolytic oxygen sensors for carbon potential calculation, has demonstrated the power of this analytical device for controlling furnace atmospheres in most heat treating applications. The electrolyte of choice for this application, is zirconia, partially stabilized with yttria. Sensor construction typically consists of an electrolyte tube, disposed inside a protective sheath which provides protection from abrasion and thermal shock; the assembly is inserted through the furnace wall. The sensing portion is at the very tip of the tube, at the junction of electrolyte, atmosphere and sensing electrode. An inner, positive electrode, bathed in air and in contact with the inner zirconia surface, provides a fixed reference point against which the outer composition is measured. The outer, (negative) electrode completes the electrochemical cell and displays a voltage that is logarithmically related to the furnace atmosphere oxygen composition. Thermodynamic relationships have been derived which provide a predictably precise relationship between the sensor voltage and the carbon potential in conventional furnace atmospheres at temperatures between 1400° F. and 2100° F.

Current commercial versions of the zirconia sensor can be differentiated by the type of outer electrode constructions used for measuring the voltage generated at the sensing surface. The first of these can be described as an "area contact electrode". One of the earliest examples of this type is a sprayed porous layer of refractory chrome nickel alloy applied to the sensing tip of a long (600 mm) zirconia tube and connected to the measuring circuit by a ceramic-protected alloy wire. This electrode proves to be eminently satisfactory in the relatively benign atmospheres from endothermic generators and other low carbon atmospheres at moderate temperatures. It suffers, however, from massive accelerated attack at higher temperatures (above about 1700° F.) and elevated carbon potential levels. Embrittlement, in combination with a mismatch in thermal coefficients of expansion, causes the sprayed alloy electrode to 'peel' off the zirconia substrate, resulting in premature failure. Attack by fumes from molten salt quench processing causes dramatic acceleration of this failure. In addition, unusual dynamic behavior has been observed with this construction, and ascribed to "catalytic" activity.

Another example of the area contact electrode consists of direct contact of a flat ended zirconia substrate with, either an alloy mesh or plate, inside the end of the protective alloy sheath. This version displays significant improvement in resistance to extreme conditions. It provides, however, many tiny pockets where carbon can accumulate. This can, in some cases, cause an elevated reading, not typical of the actual furnace atmosphere.

Another common electrode of the area contact type was developed to reduce the cost of the sensing electrolyte, which is a significant part of the sensor price. The substrate manufacturer has tried to address this expense by limiting the amount of zirconia in the sensing element. This is achieved by cementing a small cylindrical plug of zirconia into the end of a long alumina support tube using a "eutectic" ceramic cement. The flat end of this plug is then seated into a small cavity in the tip of the protective sheath, which becomes the sensing electrode. While this provides a functionally satisfactory sensor, the cemented joint is prone to develop cracks, due to temperature cycling to which it is exposed in the typical application. Every sensor of this type can be shown to leak to some extent, although the leakage is acceptably small in 'new' sensors. At some stage however, due to temperature cycling, the leak may be so large that it will cause a low measurement of carbon potential, and correspondingly damaging overcarburization. The construction which is intended to reduce the basic cost, may thus create an ultimate loss far greater than any savings realised by the cost savings.

The second type of electrode used in a commercial sensor can be described as a "line contact electrode". An end cap is positioned inside the end of an alloy protective sheath; the cap has a hole with several grooves provided axially in the walls of the hole. A round bottom zirconia tube which has a larger diameter than the hole, is seated in the hole, spring loaded and making interrupted line contact with the edge of the hole. The cap, which is welded into the sheath, is thus the line contact electrode. This type of electrode solves many of the problems listed with the area contact electrodes. It can, however, cause electrolyte fracture due in part to the spring force induced tensile stress concentration at the line of contact with the electrode, and initiated by thermal stress induced by the rapidly changing temperature gradients normally encountered in the heat treating processes, and unrestricted by the large openings in the sheath near the electrode.

An important factor addressed by this patent relates to the openings provided in the protective sheath of commercial probes to facilitate contact with the furnace atmosphere. These have, in some designs, been made both numerous, and large, in the interest of promoting good contact of the atmosphere with the sensing surface, hence, rapid response to changes in the atmosphere. Experience has shown that diffusion rates are proportional to the absolute temperature, and that not only is such openness not essential to fast response, it doesn't impede exposure to temperature effects, and can cause some totally unexpected problems, related to effective maintenance. The techniques we have pioneered over the past twenty years for maintaining a carbon sensor free of the damaging effects of soot involve two concurrent operations: 1) air is pumped into the probe annulus to oxidize the fluffy carbon deposited therein and 2) the electrodes are shorted out to cause oxygen ions to flow through the zirconia substrate and emerge as nacent oxygen, which will consume the more tenacious carbon deposited on the sensing surface. The large sheath openings in some current commercial devices, require excessive air to be pumped into the annulus in order to provide adequate oxygen for combustion of the soot. The carbon potential in the furnace can accordingly drop significantly, resulting in parts decarburization.

SUMMARY OF THE INVENTION

The principal object of this invention is to provide a practical sensing electrode design which addresses the problems relating to premature failure of commercial oxygen sensors. Further, design considerations will be established to reduce the negative impact of sensor maintenance on the production process. The problem of temperature induced stress failure of the sensing substrate in line contact electrodes is effectively eliminated by providing a virtual point contact electrode. The contamination effect found in surface contact electrodes is similarly minimized, and contrary to belief, the internal resistance is reproducibly low and on the same order of magnitude as existing probes.

The preferred maintenance routine for carbon sensors involves pumping air to the annulus between the electrolyte and the protective sheath. Essential to successfully eliminating soot or carbon deposits in the annulus and sensing surface, is establishing sufficient oxygen to this area during burnoff. This can only happen if the sensor output is reduced to levels on the order of 200 millivolts. With the exceptionally large openings of current commercial designs, most of the air admitted to the sensing area is almost immediately consumed by the furnace atmosphere. It thus requires extremely large burnoff air flow rates to increase the oxygen concentration at the sensing electrode. To counter this disadvantage, probes constructed according to this patent have smaller diameter holes located close to the sensing point. To further increase burnoff air velocity, the inside diameter of the protective sheath is reduced to provide an annular area less than half that of conventional probes. Because of the reduced internal volume, the design has the further advantage of reducing the time necessary for the probe reading to return to equilibrium after a burnoff procedure has been conducted.

DESCRIPTION OF THE PREFERRED EMBODIMENTS

Figure 1:
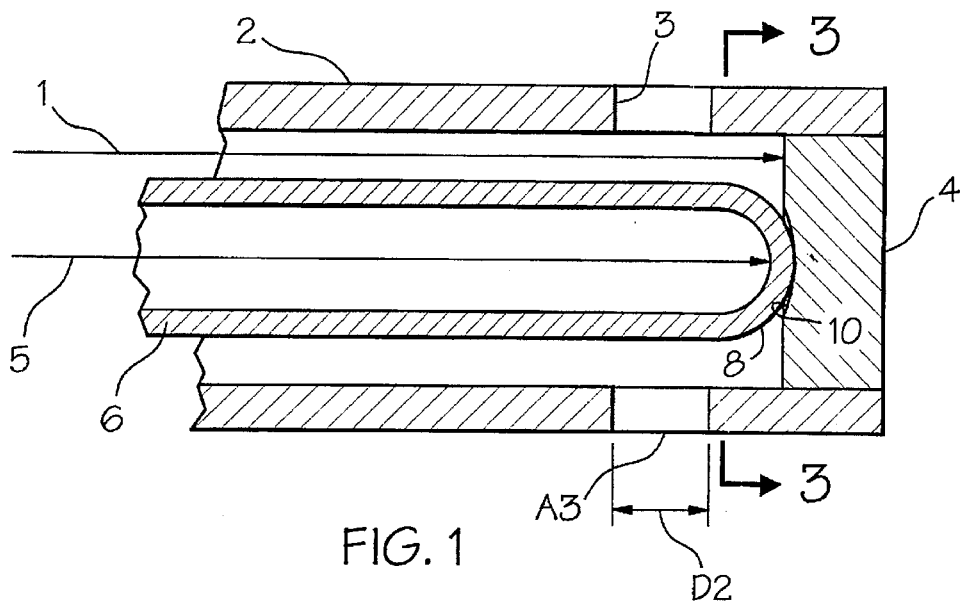
FIG. 1 is a sectional view of the sensing end of the subject probe showing only the elements described in the following specification.
Figure 2:
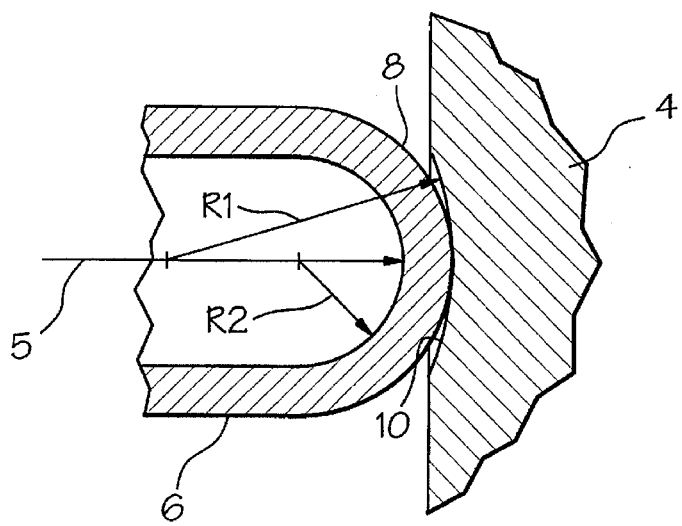
FIG. 2 is an enlarged sectional view of the tip of the sensing end shown in FIG. 1.
Figure 3:
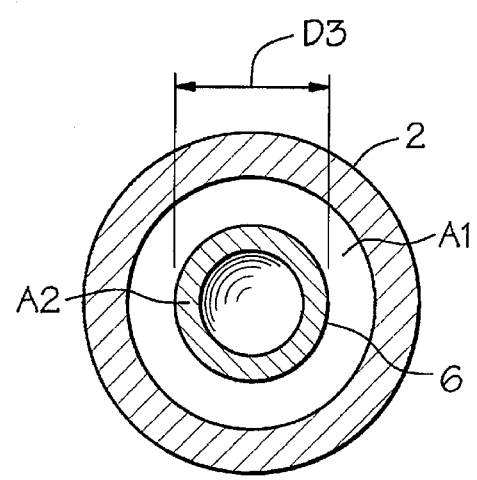
FIG. 3 is a cross-sectional through line 2—2 in FIG. 1.

The description following is sufficiently detailed to allow those skilled in the art to apply the invention. The illustration accompanying this disclosure is used only to describe the principles involved. Application of these principles to other, related devices is necessarily limited by the law governing patents. The scope of the invention is defined by the claims appended hereto.

FIG. 5. 1 through 3 shows a tubular ceramic electrolyte body 6, with spherical end closure 8, nested in tangential apposition in a spherical cavity 10 in the end cap 4 of a nickel alloy sheath 2. The cavity 10 (or cup) has a first radius of curvature R1 greater than a second radius of curvature R2 of the spherical end closure 8 of the ceramic electrolyte body 6 which is also commonly referred to as an electrolyte. The cavity 10 thus serves both as a virtual point contact sensing electrode, and as an agent for centering the ceramic electrolyte body 6 in the alloy sheath 2. First and second conductors 1 and 5 from the sheath 2 and inner electrodes, respectively, route the measured voltage between the conductors to the measuring instrument. To minimize the entrapment of carbon in the sensing area, and provide access of the atmosphere to the electrode, the first radius of curvature R1 of the cavity 18 should in a range of about 1.1 to 2.5 and preferably in a range of be about 1.3 to 2.0 times greater than that of the second radius of curvature R2 of the ceramic electrolyte body 6 which is a zirconia tube. Zirconia tubes used in commercial sensor are normally ⅜" in diameter, but this specification pertains to tubes both smaller and larger than this nominal value. It is recognized that, in normal operation at elevated temperatures, the metal of the cavity 10 (or cup) will 'creep', or flow so as to cause the point of contact to change to an area type contact. The area thus created, however, will be very small compared to other area contact electrodes, and will vary in area with the force with which the ceramic is pressed into the cup. It will not, however, tend to trap carbon during operation, since it will conform to the smooth shape of the spherical end closure 8. Accordingly, it will not demonstrate the high carbon offset or bias common to area contact electrodes.

Because there is only compressive force applied to the tube of the electrolyte body 6, there is no localized tensile stress concentration at which thermal shock can initiate cracks in the tube, as can occur in line contact electrodes.

To reduce the impact of excessive burnoff air on the furnace atmosphere, it is desirable to provide an included annular area A1 between the ceramic tube of the electrolyte body 6 and the protective sheath 2 that is between one and two times the cross sectional area A2 as defined within and outside diameter D3 of the electrolyte body, of the ceramic tube of the electrolyte body. Further, an open area R3 of the holes 3 in the sheath 2 which communicate with the furnace atmosphere, should be no greater than the annular area A1. These limitations will impart adequate velocity to the burnoff air flow to establish the necessary oxygen to the sensor surface, without impacting unfavorably on the furnace atmosphere.

We claim:

1. An oxygen sensor for measuring gas composition in a heat treating furnace, said oxygen sensor comprising:

a tubular ceramic electrolyte with a convex end closure, said electrolyte having a tip with an inner reference surface connected to a reference electrode and an outer sensing surface in contact with a sensing electrode, said sensing electrode in substantially point contact with said outer sensing surface at said tip of said electrolyte at a point of tangency, said sensing electrode connected to a protective sheath that has an annular side wall which is spaced apart from and surrounds said electrolyte, a conductor means for transmitting a generated voltage from said electrodes to a measuring device, a plurality of communicating holes in said side wall of said sheath close to said tip of said electrolyte, said outer sensing surface is convex, said sensing electrode has a concave electrolyte contacting surface with a centrally located point contact region where said outer sensing surface of said electrolyte and said electrolyte contacting surface of said sensing electrode meet at said point of tangency, and said electrolyte contacting surface has a first radius of curvature greater than a second radius of curvature of said outer sensing surface of said electrolyte at said point of tangency.

2. An oxygen sensor as claimed in claim 1 wherein:

said first radius of curvature of said electrolyte contacting surface of said sensing electrode is between 1.1 and 2.5 times greater than said second radius of curvature of said outer sensing surface of said electrolyte at said point of tangency.

3. An oxygen sensor as claimed in claim 1 further comprising:

an annular area between said annular side wall and said tubular ceramic electrolyte a cross sectional area of said tubular ceramic electrolyte defined by an outside diameter of said tubular ceramic electrolyte; and said annular area being in a range between 1.0 to 2.0 times greater than said cross sectional area.

4. An oxygen sensor as claimed in claim 1 wherein:

said communicating holes have cross sectional hole areas which do not exceed an annular area between said annular side wall and said electrolyte.

5. An oxygen sensor as claimed in claim 1 wherein said outer sensing surface is spherical and said sensing electrode has a spherical electrolyte contacting surface.

6. An oxygen sensor as claimed in claim 5 wherein said first radius of curvature of said electrolyte contacting surface of said sensing electrode is between 1.1 and 2.5 times greater than said second radius of curvature of said outer sensing surface of said electrolyte at said point of tangency.

7. An oxygen sensor as claimed in claim 5 further comprising:

an annular area between said annular side wall and said tubular ceramic electrolyte a cross sectional area of said tubular ceramic electrolyte defined by an outside diameter of said tubular ceramic electrolyte; and said annular area being in a range between 1.0 to 2.0 times greater than said cross sectional area.

8. An oxygen sensor as claimed in claim 5 wherein:

said communicating holes have cross sectional hole areas which do not exceed an annular area between said annular side wall and said electrolyte.

* * * * *